United States Patent
Ellingsen et al.

(10) Patent No.: US 7,410,502 B2
(45) Date of Patent: Aug. 12, 2008

(54) MEDICAL PROSTHETIC DEVICES HAVING IMPROVED BIOCOMPATIBILITY

(75) Inventors: Jan Eirik Ellingsen, Bekkestua (NO); Staale Petter Lyngstadaas, Nesoddtangen (NO)

(73) Assignee: Numat AS, Rud (NO)

( * ) Notice: Subject to any disclaimer, the term of this patent is extended or adjusted under 35 U.S.C. 154(b) by 1 day.

(21) Appl. No.: 10/410,660

(22) Filed: Apr. 9, 2003

(65) Prior Publication Data
US 2004/0083006 A1  Apr. 29, 2004

Related U.S. Application Data

(60) Provisional application No. 60/375,928, filed on Apr. 25, 2002.

(30) Foreign Application Priority Data
Apr. 9, 2002  (DK) .............. PA 2002 00515

(51) Int. Cl.
*A61F 2/28* (2006.01)
*A61F 2/02* (2006.01)
*A61F 2/00* (2006.01)
*C25D 5/38* (2006.01)

(52) U.S. Cl. .......... 623/23.53; 424/423; 623/23.57; 623/23.6; 623/23.76; 623/923

(58) Field of Classification Search .......... 424/423; 623/23.5, 23.53, 23.57, 23.6, 23.76, 923
See application file for complete search history.

(56) References Cited

U.S. PATENT DOCUMENTS

| | | | |
|---|---|---|---|
| 5,045,318 A | * | 9/1991 | Tengvall et al. .......... 424/422 |
| 5,152,993 A | * | 10/1992 | Bjursten et al. .......... 424/422 |
| 5,211,663 A | * | 5/1993 | Kovacs et al. .......... 623/23.6 |
| 5,609,633 A | * | 3/1997 | Kokubo .......... 424/423 |
| 5,612,049 A | | 3/1997 | Li et al. |
| 6,190,412 B1 | | 2/2001 | Lee et al. |

FOREIGN PATENT DOCUMENTS

| | | |
|---|---|---|
| EP | 0 520 721 A3 | 12/1992 |
| WO | WO-9727821 A1 | 8/1997 |
| WO | WO-98/35920 A1 | 8/1998 |
| WO | WO 00/38753 A1 | 7/2000 |
| WO | WO 00/72777 A1 | 12/2000 |
| WO | WO 02/45764 A1 | 6/2002 |

OTHER PUBLICATIONS

Tengvall, P et al. "Physico-chemical considerations of titanium as a biomaterial." *Clinical Materials* 9:115-134 (1992).
Ellingsen et al., Materials in Clinical Applications, 1995, pp. 543-550.
Arsov et al., J. Electrochem. Soc., vol. 138, No. 10, Oct. 1991, pp. 2964-2970.
S. K. Yen et al., *Biomaterials* (2001) 22(2), 125-133.

* cited by examiner

*Primary Examiner*—Thomas J Sweet
(74) *Attorney, Agent, or Firm*—Birch, Stewart, Kolasch & Birch, LLP

(57) ABSTRACT

The invention relates to a medical prosthetic device having a metal material, such as titanium or an alloy thereof, where the surface parts of the metal material are coated with a layer of a corresponding hydroxide material, such as titanium hydroxide. Preferably, the hydroxide layer includes one or more biomolecule substances associated therewith. The invention also relates to an electrolytic process for the preparation of a medical prosthetic device.

44 Claims, No Drawings

MEDICAL PROSTHETIC DEVICES HAVING IMPROVED BIOCOMPATIBILITY

RELATED APPLICATIONS

The present application claims priority from the Danish application serial no. PA 2002 00515 filed on Apr. 9, 2002 and from U.S. provisional patent application Ser. No. 60/375,928, filed on Apr. 25, 2002. All of the above applications are expressly incorporated herein by reference.

FIELD OF THE INVENTION

The present invention concerns medical prosthetic devices having improved biocompatibility.

BACKGROUND OF THE INVENTION

It has been proposed to improve the biocompatibility of metal prostheses such as a titanium prosthesis by modifying the metal surfaces thereof, e.g. by plasma bombardment, etching or electrolysis.

Anodic oxidation has been described for the formation of a thick oxide layer (i.e. thicker than the naturally occurring oxide layer) on an implant surface. For instance, WO 00/72777 describes an electrolytic oxidation process wherein an implant is immersed in an acidic electrolyte and the implant (anode) is brought into contact with an electric energy source connected to a counter-electrode (cathode) immersed in the same acidic electrolyte.

It has also been proposed to improve the biocompatibility of prostheses and implants by binding or integrating various active biomolecules to the surface of the prosthesis, e.g. on to the metallic surface of a titanium prosthesis. It has been the aim with implants prepared this way that they have improved fit; exhibit increased tissue stickiness and increased tissue compatibility; have a biologically active surface for increased cell growth, differentiation and maturation; exhibit reduced immunoreactivity; exhibit antimicrobial activity; exhibit increased biomineralization capabilities; result in improved wound and/or bone healing; lead to improved bone density; have reduced "time to load" and cause less inflammation.

Such binding has often been carried out using for example chemical reactants having two reactive functionalities such as formalin or glutaraldehyde, but the reactive nature of these agents often leads to the biomolecules becoming biologically inactive and/or with enhanced immunoreactivity which is undesirable.

SUMMARY OF THE INVENTION

It has now been found that a metal prosthetic device having a coating of a corresponding metal hydroxide on metal parts thereof exhibit advantageous structural and biocompatibility properties, and that it is possible to prepare such a device by electrolysis.

Therefore, in a first aspect, the invention concerns a medical prosthetic device comprising a metal material (A) selected from the group consisting of titanium or an alloy thereof, zirconium or an alloy thereof, tantalum or an alloy thereof, hafnium or an alloy thereof, niobium or an alloy thereof and a chromium-vanadium alloy, wherein surface parts of the metal material (A) are coated with a layer of a corresponding hydroxide material (B) selected from titanium hydroxide, zirconium hydroxide, tantalum hydroxide, hafnium hydroxide, niobium hydroxide and chromium and/or vanadium hydroxide, respectively.

In a second aspect, the invention concerns a method for preparing such a medical prosthetic device, said method comprising subjecting surface parts of the metal material (A) to an electrolysis treatment under conditions that facilitate formation of metal hydroxide to form the layer of hydroxide material (B).

It has furthermore been found that it is possible to interlock, bind, trap and/or integrate a wide variety of biomolecules in or with a hydroxide layer during the inorganic process of formation of such a hydroxide layer on metals by electrolysis. Prior to this observation, it was considered very difficult to bind and stabilize unmodified, bioactive biomolecules on metals, especially for use as bioactive surfaces on metals for use as implants in the vertebrate body in vivo.

Therefore, a preferred embodiment of the invention concerns a medical prosthetic device comprising a metal material (A) selected from the group consisting of titanium or an alloy thereof, zirconium or an alloy thereof, tantalum or an alloy thereof, hafnium or an alloy thereof, niobium or an alloy thereof and a chromium-vanadium alloy, wherein surface parts of the metal material (A) are coated with a layer of a corresponding hydroxide material (B) selected from titanium hydroxide, zirconium hydroxide, tantalum hydroxide, hafnium hydroxide, niobium hydroxide and chromium and/or vanadium hydroxide, respectively, said layer of hydroxide material (B) comprising one or more biomolecule substances (C) associated therewith.

Further, the invention concerns a method for preparing a medical prosthetic device according to the above preferred embodiment, said method comprising subjecting surface parts of the metal material (A) to an electrolysis treatment to form the layer of hydroxide material (B), said electrolysis treatment being carried out in the presence of one or more biomolecule substances (C) under conditions that render the biomolecule negatively charged.

DETAILED DESCRIPTION OF THE INVENTION

In the present context, the term "medical prosthetic device" includes within its scope any device intended to be implanted into the body of a vertebrate animal, in particular a mammal such as a human.

Medical prosthetic devices are herein also referred to as (medical) implants.

Non-limiting examples of such devices are medical devices that replaces anatomy and/or restores a function of the body such as the femoral hip joint; the femoral head; acetabular cup; elbow including stems, wedges, articular inserts; knee, including the femoral and tibial components, stem, wedges, articular inserts or patellar components; shoulders including stem and head; wrist; ankles; hand; fingers; toes; vertebrae; spinal discs; artificial joints; dental implants; ossiculoplastic implants; middle ear implants including incus, malleus, stapes, incus-stapes, malleus-incus, malleus-incus-stapes; cochlear implants; orthopaedic fixation devices such as nails, screws, staples and plates; heart valves; pacemakers; catheters; vessels; space filling implants; implants for retention of hearing aids; implants for external fixation; and also intrauterine devices (IUDs); and bioelectronic devices such as intracochlear or intracranial electronic devices.

Generally, a medical implant is composed of one or several implant parts. For instance, a dental implant usually comprises a dental fixture coupled to secondary implant parts, such as an abutment and/or a restoration tooth. However, any device, such as a dental fixture, intended for implantation may alone be referred to as an implant even if other parts are to be connected thereto.

As used herein the term "surface parts" refers to at least one defined surface region of an implant. Thus, the surface parts may include the entire surface area of the implant or portions thereof.

An example of implant surface parts intended for implantation into bone tissue is the surface of a dental fixture that is intended for implantation into the jawbone of a patient and to be in contact with bone tissue.

Another example of implant surface parts intended for implantation into bone tissue is the surface of a hip joint implant that is intended for implantation into the neck of the femur of a patient.

As used herein "for implantation into bone tissue" refers to implants intended for at least partial implantation into bone tissue, such as dental implants, orthopaedic implants, and the like. An implant for implantation into bone tissue may also be referred to as a bone tissue implant.

In the present context, the term "biomolecule" is intended to cover and comprise within its meaning a very wide variety of biologically active molecules in the widest sense of the word, be they natural biomolecules (i.e. naturally occurring molecules derived from natural sources), synthetic biomolecules (i.e. naturally occurring molecules prepared synthetically as well as non-naturally occurring molecules or forms of molecules prepared synthetically) or recombinant biomolecules (i.e. prepared through the use of recombinant techniques).

A non-limiting list of main groups of and species biomolecules that are contemplated as being suitable for incorporation into a metal hydroxide layer (in a stable and/or physiologically reversible manner) in accordance with the invention is given below.

Extracted Biomolecules:

Bioadhesives:
Fibrin; fibroin; Mytilus edulis foot protein (mefp1, "mussel adhesive protein"); other mussel's adhesive proteins; proteins and peptides with glycine-rich blocks; proteins and peptides with poly-alanine blocks; and silks.

Cell Attachment Factors:
Cell attachment factors are biomolecules that mediate attachment and spreading of cells onto biological surfaces or other cells and tissues. This group of molecules typically contains molecules participating in cell-matrix and cell-cell interaction during vertebrate development, neogenesis, regeneration and repair. Typical biomolecules in this class are molecules on the outer surface of cells like the CD class of receptors on white blood cells, immunoglobulins and haemagglutinating proteins, and extracellular matrix molecules/ligands that adhere to such cellular molecules. Typical examples of cell attachment factors with potential for use as bioactive coating on metal hydroxide-coated implants are: Ankyrins; cadherins (Calcium dependent adhesion molecules); connexins; dermatan sulphate; entactin; fibrin; fibronectin; glycolipids; glycophorin; glycoproteins; heparan sulphate; heparin sulphate; hyaluronic acid; immunoglobulins; keratan sulphate; integrins; laminins; N-CAMs (Calcium independent Adhesive Molecules); proteoglycans; spektrin; vinculin; and vitronectin.

Biopolymers:
Biopolymers are any biologically prepared molecule which, given the right conditions, can be assembled into polymeric, macromolecular structures. Such molecules constitute important parts of the extracellular matrix where they participate in providing tissue resilience, strength, rigidity, integrity etc. Some important biopolymers with potential for use as bioactive coating on metal hydroxide-coated implants are: Alginates; Amelogenins; cellulose; chitosan; collagen; gelatins; oligosaccharides; pectin.

Blood proteins:
This class of proteins typically contains any dissolved or aggregated protein which normally is present whole blood. Such proteins can participate in a wide range of biological processes like inflammation, homing of cells, clotting, cell signaling, defence, immune reactions, metabolism etc. Typical examples with potential for use as bioactive coating on metal hydroxide-coated implants are: Albumin; albumen; cytokines; factor IX; factor V; factor VII; factor VIII; factor X; factor XI; factor XII; factor XIII; hemoglobins (with or without iron); immunoglobulins (antibodies); fibrin; platelet derived growth factors (PDGFs); plasminogen; thrombospondin; and transferrin.

Enzymes:
Enzymes are any protein or peptide that have a specific catalytic effect on one ore more biological substrates which can be virtually anything from simple sugars to complex macromolecules like DNA. Enzymes are potentially useful for triggering biological responses in the tissue by degradation of matrix molecules, or they could be used to activate or release other bioactive compounds in the implant coating. Some important examples with potential for use as bioactive coating on metal hydroxide-coated implants are: Abzymes (antibodies with enzymatic capacity); adenylate cyclase; alkaline phosphatase; carboxylases; collagenases; cyclooxygenase; hydrolases; isomerases; ligases; lyases; metallo-matrix proteases (MMPs); nucleases; oxidoreductases; peptidases; peptide hydrolase; peptidyl transferase; phospholipase; proteases; sucrase-isomaltase; TIMPs; and transferases.

Extracellular Matrix Proteins and Biomolecules
Specialized cells, e.g fibroblasts and osteoblasts, produce the extracellular matrix. This matrix participates in several important processes. The matrix is crucial for i.e. wound healing, tissue homeostasis, develoment and repair, tissue strength, and tissue integrity. The matrix also decides the extracellular milieu like pH, ionic strength, osmolarity etc. Furthermore, extracellular matrix molecules are crucial for induction and control of biomineral formation (e.g. bone, cartilage, and teeth). Important extracellular proteins and biomolecules with potential for use as bioactive coating on metal hydroxide-coated implants include: Ameloblastin; amelin; amelogenins; collagens (I to XII); dentin-sialo-protein (DSP); dentin-sialo-phospho-protein (DSPP); elastins; enamelin; fibrins; fibronectins; keratins (1 to 20); laminins; tuftelin; carbohydrates; chondroitin sulphate; heparan sulphate; heparin sulphate; hyaluronic acid; lipids and fatty acids; lipopolysaccarides.

Growth Factors and Hormones:
Growth factors and hormones are molecules that bind to cellular surface structures (receptors) and generate a signal in the target cell to start a specific biological process. Examples of such processes are growth, programmed cell death, release of other molecules (e.g. extracellular matrix molecules or sugar), cell differentiation and maturation, regulation of metabolic rate etc. Typical examples of such biomolecules with potential for use as bioactive coating on metal hydroxide-coated implants are: Activins (Act); Amphiregulin (AR); Angiopoietins (Ang 1 to 4); Apo3 (a weak apoptosis inducer also known as TWEAK, DR3, WSL-1, TRAMP or LARD); Betacellulin (BTC); Basic Fibroblast Growth Factor (bFGF, FGF-b); Acidic Fibroblast Growth Factor (aFGF, FGF-a); 4-1BB Ligand; Brain-derived Neurotrophic Factor (BDNF); Breast and Kidney derived Bolokine (BRAK); Bone Morphogenic Proteins (BMPs); B-Lymphocyte Chemoattractant/B cell Attracting Chemokine 1 (BLC/BCA-1); CD27L (CD27 ligand); CD30L (CD30 ligand); CD40L (CD40 ligand); A Proliferation-inducing Ligand (APRIL); Cardiotrophin-1 (CT-1); Ciliary Neurotrophic Factor (CNTF); Connective Tissue Growth Factor (CTGF); Cytokines; 6-cysteine Chemokine (6Ckine); Epidermal Growth Factors (EGFs); Eotaxin (Eot); Epithelial Cell-derived Neutrophil Activating Protein 78 (ENA-78); Erythropoietin (Epo); Fibroblast Growth Factors (FGF 3 to 19); Fractalkine; Glial-derived Neurotrophic Factors (GDNFs); Glucocorticoid-induced TNF Receptor Ligand (GITRL); Granulocyte Colony Stimulating Factor (G-CSF); Granulocyte Macrophage Colony Stimulating Factor (GM-CSF); Granulocyte Chemotactic Proteins (GCPs); Growth Hormone (GH); I-309; Growth Related Oncogene (GRO); Inhibins (Inh); Interferon-inducible T-cell Alpha Chemoattractant (I-TAC); Fas Ligand (FasL); Heregulins (HRGs); Heparin-Binding Epidermal Growth Factor-Like Growth Factor (HB-EGF); fms-like Tyrosine Kinase 3 Ligand (Flt-3L); Hemofiltrate CC Chemokines (HCC-1 to 4); Hepatocyte Growth Factor (HGF); Insulin; Insulin-like Growth Factors (IGF 1 and 2); Interferon-gamma Inducible Protein 10 (IP-10); Interleukins (IL 1 to 18); Interferon-gamma (IFN-gamma); Keratinocyte Growth Factor (KGF); Keratinocyte Growth Factor-2 (FGF-10); Leptin (OB); Leukemia Inhibitory Factor (LIF); Lymphotoxin Beta (LT-B); Lymphotactin (LTN); Macrophage-Colony Stimulating Factor (M-CSF); Macrophage-derived Chemokine (MDC); Macrophage Stimulating Protein (MSP); Macrophage Inflammatory Proteins (MIPs); Midkine (MK); Monocyte Chemoattractant Proteins (MCP-1 to 4); Monokine Induced by IFN-gamma (MIG); MSX 1; MSX 2; Mullerian Inhibiting Substance (MIS); Myeloid Progenitor Inhibitory Factor 1 (MPIF-1); Nerve Growth Factor (NGF); Neurotrophins (NTs); Neutrophil Activating Peptide 2 (NAP-2); Oncostatin M (OSM); Osteocalcin; OP-1; Osteopontin; OX40 Ligand; Platelet derived Growth Factors (PDGF aa, ab and bb); Platelet Factor 4 (PF4); Pleiotrophin (PTN); Pulmonary and Activation-regulated Chemokine (PARC); Regulated on Activation, Normal T-cell Expressed and Secreted (RANTES); Sensory and Motor Neuron-derived Factor (SMDF); Small Inducible Cytokine Subfamily A Member 26 (SCYA26); Stem Cell Factor (SCF); Stromal Cell Derived Factor 1 (SDF-1); Thymus and Activation-regulated Chemokine (TARC); Thymus Expressed Chemokine (TECK); TNF and ApoL-related Leukocyte-expressed Ligand-1 (TALL-1); TNF-related Apoptosis Inducing Ligand (TRAIL); TNF-related Activation Induced Cytokine (TRANCE); Lymphotoxin Inducible Expression and Competes with HSV Glycoprotein D for HVEM T-lymphocyte receptor (LIGHT); Placenta Growth Factor (PlGF); Thrombopoietin (Tpo); Transforming Growth Factors (TGF alpha, TGF beta 1, TGF beta 2); Tumor Necrosis Factors (TNF alpha and beta); Vascular Endothelial Growth Factors (VEGF-A, B, C and D); calcitonins; and steroid compounds such as naturally occurring sex hormones such as estrogen, progesterone, testosterone as well as analogues thereof. Thus, certain implants such as IUD's (intrauterine devices) comprising e.g. estrogens or progesterone or analogues thereof could be contemplated.

Nucleic Acids (DNA):

DNA encodes the genes for proteins and peptides. Also, DNA contains a wide array of sequences that regulate the expression of the contained genes. Several types of DNA exist, depending on source, function, origin, and structure. Typical examples for DNA based molecules that can be utilized as bioactive, slow release coatings on implants (local gene-therapy) are: A-DNA; B-DNA; artificial chromosomes carrying mammalian DNA (YACs); chromosomal DNA; circular DNA; cosmids carrying mammalian DNA; DNA; Double-stranded DNA (dsDNA); genomic DNA; hemi-methylated DNA; linear DNA; mammalian cDNA (complimentary DNA; DNA copy of RNA); mammalian DNA; methylated DNA; mitochondrial DNA; phages carrying mammalian DNA; phagemids carrying mammalian DNA; plasmids carrying mammalian DNA; plastids carrying mammalian DNA; recombinant DNA; restriction fragments of mammalian DNA; retroposons carrying mammalian DNA; single-stranded DNA (ssDNA); transposons carrying mammalian DNA; T-DNA; viruses carrying mammalian DNA; and Z-DNA.

Nucleic Acids (RNA):

RNA is a transcription of DNA-encoded information. (Sometimes (in some viruses) RNA is the essential information-encoding unit). Besides being an intermediate for expression of genes, RNA have been shown to have several biological functions. Ribozymes are simple RNA molecules with a catalytic action. These RNA can catalyze DNA and RNA cleavage and ligation, hydrolyse peptides, and are the core of the translation of RNA into peptides (the ribosome is a ribozyme). Typical examples of RNA molecules with potential for use as bioactive coating on metal hydroxide-coated implants are: Acetylated transfer RNA (activated tRNA, charged tRNA); circular RNA; linear RNA; mammalian heterogeneous nuclear RNA (hnRNA), mammalian messenger RNA (mRNA); mammalian RNA; mammalian ribosomal RNA (rRNA); mammalian transport RNA (tRNA); mRNA; polyadenylated RNA; ribosomal RNA (rRNA); recombinant RNA; retroposons carrying mammalian RNA; ribozymes; transport RNA (tRNA); viruses carrying mammalian RNA; short inhibitory RNA (siRNA).

Receptors:

Receptors are cell surface biomolecules that bind signals (e.g. hormone ligands and growth factors) and transmit the signal over the cell membrane and into the internal machinery of cells. Different receptors are differently "wired" imposing different intracellular responses even to the same ligand. This makes it possible for the cells to react differentially to external signals by varying the pattern of receptors on their surface. Receptors typically bind their ligand in a reversible manner, making them suitable as carriers of growth factors that are to be released into the tissue. Thus by coating implants with growth factor receptors, and then load these receptors with their principal ligands, a bioactive surface is achieved that can be used for controlled release of growth factors to the surrounding tissues following implantation. Examples of suitable receptors with potential for use as bioactive coating on metal hydroxide-coated implants includes: The CD class of receptors CD; EGF receptors; FGF receptors; Fibronectin receptor (VLA-5); Growth Factor receptor, IGF Binding Proteins (IGFBP 1 to 4); Integrins (including VLA 1-4); Laminin receptor; PDGF receptors; Transforming Growth Factor alpha and beta receptors; BMP receptors; Fas; Vascular Endothelial Growth Factor receptor (Flt-1); Vitronectin receptor.

Synthetic Biomolecules

Synthetic biomolecules are molecules that are based on (mimicking) naturally occurring biomolecules. By synthesizing such molecules a wide array of chemical and structural modification can be introduced that can stabilize the molecule or make it more bioactive or specific. Thus if a molecule is either too unstable or unspecific to be used from extracts it is possible to engineer them and synthesize them for use as implant surface coatings. Furthermore, many biomolecules are so low abundant that extraction in industrial scales is impossible. Such rare biomolecules have to be prepared synthetically, e.g. by recombinant technology or by (bio-) chemistry. Below is listed several classes of synthetic molecules that can be potentially useful for implant coatings:

Synthetic DNA:

A-DNA; antisense DNA; B-DNA; complimentary DNA (cDNA); chemically modified DNA; chemically stabilized DNA; DNA; DNA analogues ; DNA oligomers; DNA polymers; DNA-RNA hybrids; double-stranded DNA (dsDNA); hemi-methylated DNA; methylated DNA; single-stranded DNA (ssDNA); recombinant DNA; triplex DNA; T-DNA; Z-DNA.

Synthetic RNA:

Antisense RNA; chemically modified RNA; chemically stabilized RNA; heterogeneous nuclear RNA (hnRNA); messenger RNA (mRNA); ribozymes; RNA; RNA analogues; RNA-DNA hybrids; RNA oligomers; RNA polymers; ribosomal RNA (rRNA); transport RNA (tRNA); short inhibitory RNA (siRNA).

Synthetic Biopolymers:

Cationic and anionic liposomes; cellulose acetate; hyaluronic acid; polylactic acid; polyglycol alginate; polyglycolic acid; poly-prolines; polysaccharides.

Synthetic Peptides:

Decapeptides comprising DOPA and/or diDOPA; peptides with sequence "Ala Lys Pro Ser Tyr Pro Pro Thr Tyr Lys"; peptides where Pro is substituted with hydroxyproline; peptides where one or more Pro is substituted with DOPA; peptides where one or more Pro is substituted with di-DOPA; peptides where one or more Tyr is substituted with DOPA; peptide hormones; peptide sequences based on the above listed extracted proteins; peptides comprising an RGD (Arg Gly Asp) motif.

Recombinant Proteins:

All recombinantly prepared peptides and proteins.

Synthetic Enzyme Inhibitors:

Synthetic enzyme inhibitors range from simple molecules, like certain metal ions, that block enzyme activity by binding directly to the enzyme, to synthetic molecules that mimic the natural substrate of an enzyme and thus compete with the principle substrate. An implant coating including enzyme inhibitors could help stabilizing and counteract breakdown of other biomolecules present in the coating, so that more reaction time and/or higher concentration of the bioactive compound is achieved. Examples of enzyme inhibitors are: Pepstatin; poly-prolines; D-sugars; D-aminocaids; Cyanide; Diisopropyl fluorophosphates (DFP); metal ions; N-tosyl-1-phenylalaninechloromethyl ketone (TPCK); Physostigmine; Parathion; Penicillin.

Vitamins (Synthetic or Extracted) for Incorporation in Hydroxide:

Biotin; calciferol (Vitamin D's; vital for bone mineralisation); citrin; folic acid; niacin; nicotinamide; nicotinamide adenine dinucleotide (NAD, NAD+); nicotinamide adenine dinucleotide phosphate (NADP, NADPH); retinoic acid (vitamin A); riboflavin; vitamin B's; vitamin C (vital for collagen synthesis); vitamin E; vitamin K's.

Other Bioactive Molecules for Incorporation into Hydroxide Coatings

Adenosine di-phosphate (ADP); adenosine monophosphate (AMP); adenosine tri-phosphate (ATP); amino acids; cyclic AMP (cAMP); 3,4-dihydroxyphenylalanine (DOPA); 5'-di(dihydroxyphenyl-L-alanine (diDOPA); diDOPA quinone; DOPA-like o-diphenols; fatty acids; glucose; hydroxyproline; nucleosides; nucleotides (RNA and DNA bases); prostaglandin; sugars; sphingosine 1-phosphate; rapamycin; synthetic sex hormones such as estrogen, progesterone or testosterone analogues, e.g. Tamoxifene; estrogen receptor modulators (SERMs) such as Raloxifene; bis-phosphonates such as alendronate, risendronate and etidronate; statins such as cerivastatin, lovastatin, simvaststin, pravastatin, fluvastatin, atorvastatin and sodium 3,5-dihydroxy-7-[3-(4-fluorophenyl)-1-(methylethyl)-1H-indol-2-yl]-hept-6-enoate.

Drugs for Incorporation into Hydroxide Coatings

Drugs incorporated in the hydroxide layer could be utilized for local effects like improving local resistance against invading microbes, local pain control, local inhibition of prostaglandin synthesis; local inflammation regulation, local induction of biomineralisation and local stimulation of tissue growth. Examples of drugs suitable for incorporation into metal hydroxide layers include: Antibiotics; cyclooxygenase inhibitors; hormones; inflammation inhibitors; NSAID's (non-steroid antiinflammatory agents); painkillers; prostaglandin synthesis inhibitors; steroids, tetracycline (also as biomineralizing agent).

Biologically Active Ions for Incorporation in Hydroxide Coatings

Ions are important in a diversity of biological mechanisms. By incorporating biologically active ions in metal hydroxide layers on implants it is possible to locally stimulate biological processes like enzyme function, enzyme blocking, cellular uptake of biomolecules, homing of specific cells, biomineralization, apoptosis, cellular secretion of biomolecules, cellular metabolism and cellular defense. Examples of bioactive ions for incorporation into metal hydroxide include: Calcium; chromium; copper; fluoride; gold; iodide; iron; potassium; magnesium; manganese; selenium; sulphur; stannum (tin); silver; sodium; zinc; nitrate; nitrite; phosphate; chloride; sulphate; carbonate; carboxyl; oxide.

Marker Biomolecules

Biological Markers are molecules that generates a detectable signal, e.g. by light emission, enzymatic activity, radioactivity, specific colour, magnetism, X-ray density, specific structure, antigenicity etc., that can be detected by specific instruments or assays or by microscopy or an imaging method like x-ray or nuclear magnetic resonance. Markers are used to monitor biological processes in research and development of new biomedical treatment strategies. On implants, such markers would typically be employed to monitor processes like biocompatibility, formation of tissue, tissue neogenesis, biomineralisation, inflammation, infection, regeneration, repair, tissue homeostasis, tissue breakdown, tissue turnover, release of biomolecules from the implant surface, bioactivity of released biomolecules, uptake and expression of nucleic acids released from the implant surface, and antibiotic capability of the implant surface to provide "proof of principle", effect, efficacy and safety validation prior to clinical studies.

Marker biomolecules suitable for incorporation in hydroxide coatings include: Calcein; alizaran red; tetracyclins; fluorescins; fura; luciferase; alkaline phosphatase; radiolabeled aminoacids (e.g. marked with $^{32}P$, $^{33}P$, $^{3}H$, $^{35}S$, $^{14}C$, $^{125}I$, $^{51}Cr$, $^{45}Ca$); radiolabeled nucleotides (e.g. marked with $^{32}P$, $^{33}P$, $^{3}H$, $^{35}S$, $^{14}C$,); radiolabeled peptides and proteins; radiolabeled DNA and RNA; immuno-gold complexes (gold particles with antibodies attached); immuno-silver complexes; immuno-magnetite complexes; Green Fluorescent protein (GFP); Red Fluorescent Protein (E5); biotinylated proteins and peptides; biotinylated nucleic acids; biotinylated antibodies; biotinylated carbon-linkers; reporter genes (any gene that generates a signal when expressed); propidium iodide; diamidino yellow.

The device according to the invention can be used for a number of purposes. Examples of such purposes include use for: inducing local hard tissue (e.g. bone tissue) formation at the implantation site; controlling microbial growth and/or invasion at the implantation site or systemically; reducing inflammation at the implantation site or systemically; stimulating ligament repair, regeneration or formation; inducing cartilage formation; nucleating, controlling and/or templating biomineralization; improving attachment between implants and tissues; improving osseointegration of implants; improving tissue adherence to an implant; hindering tissue adherence to an (semi-permanent or temporary) implant; improving contact between tissues or tissues and implants, improving tissue sealing of a (surgical) wound; inducing apoptosis (cell death) in unwanted cells (e.g. cancer cells); inducing specific cell differentiation and/or maturation, increasing tissue tensile strength; improving wound healing; speeding up wound healing; templating tissue formation; guiding tissue formation; local gene therapy; stimulating nerve growth; improving vascularisation in tissues adjacent to an implant; stimulating local extracellular matrix synthesis; inhibiting local extracellular matrix breakdown; inducing local growth factor release; increasing local tissue metabolism; improving function of a tissue or body-part; reducing local pain and discomfort. The purpose will depend on the type of implant as well as the nature and/or concentration of any biomolecule present in the hydroxide layer on the implant.

When the metal material (A) is an alloy of titanium, zirconium, tantalum, hafnium or niobium, it may be an alloy between one or more of these metal elements; or it may be an alloy comprising one or more other metals such as aluminium, vanadium, chrome, cobalt, magnesium, iron, gold, silver, copper, mercury, tin or zinc; or both.

It is preferred that the metal material (A) is titanium or an alloy thereof, e.g. an alloy with zirconium, tantalum, hafnium, niobium, aluminium, vanadium, chrome, cobalt, magnesium, iron, gold, silver, copper, mercury, tin or zinc. In a particularly preferred embodiment, the metal material (A) is titanium.

The corresponding hydroxide material (B) is preferably titanium hydroxide.

As stated above, prosthetic devices having a coating of a corresponding metal hydroxide on metal parts thereof exhibit advantageous structural and biocompatibility properties. For instance, a hydroxide layer seems to be more reactive in vivo than the corresponding oxide which seems to be more stable. Thus, without being bound to any particular theory, it is contemplated that a metal hydroxide layer, to a greater extent than a metal oxide layer, will promote interaction with endogenous calcium phosphate because of the increased in vivo reactivity and in that way improved osseointegration in comparison with an implant covered with the more inert oxide.

Preferably, the layer of hydroxide material comprises one or more biomolecule substances associated therewith. Suitable biomolecules are listed above. In this context, it shall be noted that the hydroxide layer may be formed to provide an in vivo controlled release of the biomolecule(s) associated therewith.

The biomolecule substance(s) may be present on the surface of the hydroxide material, present as an inclusion compound and/or trapped in the hydroxide material.

Preferred biomolecules for use in the present invention are biomolecules, among those listed above, having a pI (or iso-electric point) below 7.0 (i.e. having a net negative charge at pH above 7.0). It will be clear to the skilled person that the property of having a pI of below 7.0 is not limited to any particular group or sub-group of biomolecules among those listed above, but may be found in all types of biomolecules according to their origin as well as their function in the organism from which they originate.

Furthermore, the biomolecules should preferably be stable at pH above 7.0, more preferably above pH 8.0, in particular above pH 9.0. In the present context, the term "stable" is intended to mean that the biomolecule in question does not disintegrate or decompose (e.g. RNA will disintegrate at pH above 9.0) or otherwise be functionally irreversibly destroyed at the pH ranges indicated.

Preferred groups of biomolecules for use in the present invention are:

Biomolecules stimulating bone healing, such as TGFs, BMPs, amelogenin, and ameloblastin;

Biomolecules stimulating wound healing, such as VEGFs, PDGF, HGF, KGF, and FGF;

Biomolecules stimulating mineral deposition, such as ameloblastin, poly-prolines, and collagens;

Biomolecules stimulating cell attachment, such as extracellular matrix, CD molecules, integrins, and RGD-peptides;

Biomolecules stimulating bone attachment, such as extracellular matrix, CD molecules, integrins, and RGD-peptides;

Biomolecules stimulating cell proliferation, such as growth factors;

Biomolecules stimulating osteoblastic cell proliferation, such as BMP, TGF, IL-6, osteocalcin, osteoprotegrin, BSP, and cytokines;

Biomolecules stimulating cell differentiation, such as amelogenin, and growth factors; and Biomolecules stimulating osteoblastic cell differentiation, such as amelogenin, and growth factors.

The amount of biomolecule substance (C) present on or in the hydroxide layer (B) of the parts of the prosthesis, device coated with the hydroxide may vary within wide limits, e.g. dependent on the chemical and biological characteristics of the biomolecule substance or substances in question. Thus, the biomolecule substance (C) associated with the hydroxide material (B) may be present in amounts ranging from as low from 1 picogram per $mm^2$ to as high as 1 mg per $mm^2$ of hydroxide-coated implant surface. However, it is contemplated that most useful biomolecule coatings will range from 0.1 nanogram to 100 microgram per $mm^2$.

The medical prosthetic devices according to the invention, both those incorporating one or more biomolecule substance(s) (C) as well as those without such biomolecule substances, are preferably sterile.

As indicated above, the method of the invention for preparing hydroxide-coated devices involves subjecting surface parts of the metal material (A) to an electrolysis treatment at pH above 7.0 to form the hydroxide layer (B). The electrolysis conditions can be varied to produce hydroxide layers of varying roughness, porosity and thickness. At pH values below 7.0, a metal oxide layer is formed instead of a metal hydroxide layer.

Accordingly, any pH above 7.0, such as within the range of pH 7.1 to pH 14.0 can be used, but preferred pH for the preparation of a hydroxide layer comprising one or more biomolecules is within the range of pH 7.1 to 12.0, in particular within the range of pH 7.1 to 11.0, such as pH 7.1 to 10.0, for example pH 7.1 to 9.0.

A very high pH (usually above pH 12.0) will typically produce a rough (etched) underlying metallic surface, whereas low pH conditions (typically pH 7.1-10.0) will conserve the original surface topography, i.e. for instance a smooth underlying metallic surface.

As used herein the term "hydroxide layer" means a layer comprising predominantly hydroxide in comparison to the corresponding oxide.

High voltage conditions (typically between 10 V and 150 V) will produce a more porous hydroxide layer than low voltage conditions (typically below 10 V).

The time aspect is the most important for the thickness of the hydroxide layer; the longer time in electrolysis, the thicker the layer will become. However, also voltage, temperature and pH will affect the thickness of the hydroxide layer. The hydroxide layer becomes thicker if a higher voltage is applied. A higher temperature and/or a higher pH also increases the hydroxide layer thickness.

The hydroxide layer thickness may be within the range of 1 nm to 50 µm, preferably equal to or above 0.5 µm, more preferably equal to or above 1 µm, such as within the range of 1 to 20 µm, in particular within the range of 4 to 15 µm.

As further indicated above, the method of the invention for preparing hydroxide-coated devices having one or more biomolecules substances (C) associated with the hydroxide layer involves subjecting surface parts of the metal material (A) to a electrolysis treatment to form the hydroxide layer (B), said treatment being carried out in the presence of one or more biomolecule substances (C) as discussed above. It has been found that it is important that the conditions in the electrolyte (pH, ionic strength, etc) are such that the biomolecule has a net negative charge. It is therefore advantageous that the biomolecules are ampholytes, i.e. they are weak acids or bases that change their net charge according to the ionic strength and pH of the solution they are dissolved in. Consequently, the main concern for incorporation thereof in a hydroxide layer is stability under the conditions needed for bio-hydroxide preparation, i.e. an environment that supply enough OH⁻ ions for hydroxide preparation and at the same time keeps the net charge of the biomolecule in question negative. This mostly means that the electrolyte should have a low salt concentration and hence ionic strength; a comparatively high temperature, although preferably below any denaturing temperature of the biomolecule substance; and a pH above 7.0.

Thus, the electrolyte may be any salt solution, preferably aqueous, e.g. a solution of sodium chloride, sodium sulfate, calcium phosphate, calcium chloride, phosphate buffered saline (PBS), saline, a salt solution mimicking physiological conditions, bi-carbonates, carbonates etc., in which the desired biomolecule is dissolved. The ionic strength of the salt is typically 1 M, but concentrations can be adjusted to as low as 0,01 M and as high as 10 M according to the chemical properties and concentration of the biomolecule(s).

The temperature of the electrolyte comprising the biomolecule may range from freezing (0° C.) to as high as the boiling point of the electrolyte, typically around 100° C. However, when preparing a device according to the invention comprising biomolecule substance(s) (C) in the hydroxide layer, the use of temperatures in the upper part of this range clearly depends on the ability of the biomolecule substance(s) (C) present to withstand such temperatures without damage. If the biomolecule can withstand it, an optimum temperature for the formation of hydroxide is from around ambient (20° C.) to 80° C. However, if the biomolecule in question is instable at high temperatures the electrolyte can be cooled to a temperature as low as 0° C. if the pH and salt concentration is adjusted accordingly and the reaction time is increased.

The pH of the electrolyte is typically adjusted to the desired pH by means of a strong base, e.g. NaOH, KOH, etc, although it should be taken into account that a pH above 12 will produce an irregular, etched implant surface on titanium while a pH under 10 mostly conserves the original surface topography. If a device comprising biomolecule substance(s) is being prepared, the pH is adjusted according to the desired hydroxide/biomolecule ratio. High pH produces an implant surface with a high hydroxide/biomolecule ratio (=more metal hydroxide), whereas a pH closer to neutral, but not below the pI of the biomolecule in question, will produce a surface with a low hydroxide/bio-molecule ratio (=relatively more biomolecules). Accordingly, any pH above 7, such as within the range of pH 7.1 to pH 14.0 can be used, but preferred pH is within the range of pH 7.1 to 12.0, in particular within the range of pH 7.1 to 11.0, such as pH 7.1 to 10.0, for example pH 7.1 to 9.0, depending on the chemical characteristics and concentration of the biomolecule(s), the electrolyte used and the preferred hydroxide/biomolecule ratio. For higher hydroxide/biomolecule(s) ratios (=more hydroxide), pH should be adjusted to be more basic, and for lower hydroxide/biomolecule(s) ratios (=more biomolecule(s)), pH should be adjusted to be closer to, but higher than, $pI_{BIOMOLECULE}$. The only requirement is that there are hydroxide ions (OH⁻) and negatively charged biomolecules (Biomolecule⁻, net charge) present in the electrolyte.

The concentration of the biomolecule(s) (one or any combinations of two or more) in the electrolyte may vary over a very wide range, depending on type of bioactivity, type of molecule, chemical and biological characteristics, toxicity, potency, mode of action, if it is to be released or not from the hydroxide layer, stability in vivo, stability in the electrolyte, availability, optimal pH, etc., Thus, the concentration of the biomolecule(s) in the electrolyte may be within the range of 1 pg to 50 mg per milliliter. A preferred range is between 10 pg and 1 mg per milliliter, but the optimal biomolecule concentration should always be by finally determined in pilot experiments with each biomolecule or biomolecule-mix. Also, the time span over which the electrolysis is performed may vary but chiefly influences the thickness of the hydroxide layer and hence the concentration of biomolecules in the hydroxide layer.

An electrolysis cell for use in the methods of the invention may be of any conventional design but is typically a two-chamber cell without any conducting connections between the chambers except for the electrolyte. The metal implant to be hydroxide-modified is placed in the anode (i.e. the positively charged electrode) chamber whereas the cathode (the negatively charged electrode), typically made of platinum, is placed in a separate chamber. The electrolytes of each chamber are connected through a porous glass or porcelain filter allowing the current to pass unhindered but without any exchange of electrolytes between the two chambers. This is important when preparing devices comprising biomolecule substance(s) because the products from the cathode reaction could potentially interfere with the formation of the biomolecule-hydroxide layer or destroy or modify the biomolecule in the anode electrolyte. The separation of the two cells also allows the use of a smaller anode electrolyte volume and thus a more effective use of biomolecules as well as the possibility to use a two-electrolyte system that allows optimization of the electrolytic process, e.g. one electrolyte optimal for biomolecules on the anode side and an electrolyte on the cathode side which is optimized for the efficacy of the electrolysis per se (conductivity, avoiding toxic products, or even producing useful byproducts/coatings).

As indicated above, the temperature in the anode cell ($T_{an}$) should be as high at possible with an optimum for hydroxide preparation at 80° C.

The electrolytic process itself also produces heat which can pose two problems; constituents of the electrolyte will evaporate so that the volume decreases and the ionic strength and the concentration of biomolecules increase above the preferred range, and the increase in temperature might cause precipitation, coagulation, denaturation, degradation or destruction of biomolecule(s) present. Therefore, the anode compartment of the electrolysis cell is preferably equipped with a cooled lid for condensation of vaporized electrolyte and a temperature regulated radiator shell for stabilizing temperatures and volumes during electrolysis.

By adjusting current, charge and electrolyte composition it may also be possible to provide a favorable milieu for negative charge for most biomolecules. If not, a pulse field electrolysis set-up where the polarity of the electrodes is switching in controlled cycles during preparation of the bio-hydroxide layer could be one way to omit a positive net charge problem.

The power supply is typically a so-called current pump, i.e. a devicecdelivering a constant current even if the resistance within the circuit varies. Although voltages between 0,1 and 1000 volts can be used, the voltage is typically below 10 volts. The current density during electrolysis is typically in the range of 0,1 mA to 1 A per square centimeter ($cm^2$) of implant specimen. A preferred charge density is 1mA/$cm^2$ although adjustments in the electrolyte, pH and temperature to increase biomolecule compatibility may command minor or major deviations from this value.

The duration of the process depends on several parameters such as the desired thickness of the bio-hydroxide layer, the composition and characteristics of the electrolyte, the characteristics of the biomolecule, the temperature and pH, the desired hydroxide/biomolecule ratio, the size of the implant specimen, the volume of the anode electrolyte, the concentration of the biomolecule, etc. Thus, the duration of the process may be between 0.5 hours and several days. However, an optimal time-span is generally between 8 and 24 hours.

To monitor the bio-hydroxide process, a calomel electrode may typically be placed in the anode chamber. When the hydroxide layer formation process at the anode is optimal, a difference of about 1 Volt is observed between the calomel electrode and the titanium anode. If the current differs much from this value, the process will be running under sub-optimal conditions and a change in the set-up should be considered. Furthermore, a temperature probe and a pH probe may typically be placed in the anode chamber to monitor that the process is running within the desired pH and temperature limits. A stirring device such as a magnetic stirrer may also be applied in the anode cell to continuously mix the electrolyte and keep the temperature homogenous and avoid variations in local ionic strength, pH and biomolecule concentrations.

After the electrolysis step, the now biomolecule/hydroxide-coated metal implant is immediately removed from the electrolyte and treated according to the requirement of the biomolecule(s) in question. Typically, the sterile implant specimen is allowed to air-dry and is then packaged in a sterile, airtight plastic bag in which it is stored until use for implantation. However, some biomolecules might be sensitive to drying, and consequently a wet storage system might be desired, e.g. like canning or storage in a fluid like saline or simply the electrolyte from the manufacturing process. Although the electrolysis can be run under aseptic or even sterile conditions, the need for doing this may be avoided by including a sterilization step prior to use, using conventional methods such as ionizing radiation, heating, autoclaving, or ethylene oxide gas etc. The choice of method will depend on the specific characteristics and properties of the biomolecule(s) present in the metal hydroxide layer.

Generally, sterilization of medical devices is performed by autoclaving, usually at 120° C. Autoclaving of a medical prosthetic device according to the invention will not affect the hydroxide layer composition or structure.

Prior to the electrolysis treatment, the implant should be thoroughly cleaned. This may typically consist in the implant being mechanically pre-treated by electropolishing or sandblasting to modify the surface structure if desired, and subsequently thoroughly cleaned using hot caustic soda followed by a degreasing step, e.g. in concentrated trichloroethylene, ethanol or methanol, before being treated in a pickling solution, e.g. hydrofluoric acid, to remove oxides and impurities on the surface. After pickling the implant specimen is washed thoroughly in hot, double distilled, ion-exchanged water.

To produce sterile devices incorporating one or more biomolecule substance(s) (C) as well as those without such substances, the process for producing the devices can be run under sterile conditions, or the modified implant can alternatively be sterilised after completion of the process. A post-process sterilisation can be carried out by means any of the methods well known for sterilisation purposes in the field of medical devices and implants. Such methods typically involve autoclaving, heating, exposure to UV or ionising radiation, or chemical sterilisation with ethylene oxide or similar chemicals. The preferred method will depend i.a. on the presence of as well as the type and amount of biomolecule substances, as well as regulatory rules for medical devices. When dealing in particular with devices or implants incorporating one or more biomolecule substance(s) (C), it is preferred to carry out the production thereof under sterile conditions in order to interfere as little as possible with the biomolecule substances.

In a special embodiment of the invention, a metal device or implant with a two-layer or dual zone coating is prepared, whereby the device or implant is first subjected to a first electrolysis treatment as described above to form a first hydroxide layer or zone without any biomolecule substance (C), followed by a second electrolysis treatment in the presence of one or more biomolecule substance(s) (C) as described above to deposit a second hydroxide layer or zone on top of the first layer, said second layer then having biomolecule substance(s) (C) associated with it.

Another embodiment of the invention relates to a medical prosthetic device, such as a dental implant, comprising a first hydroxide zone intended to be brought into contact with soft tissue, and a second hydroxide zone intended to be brought into contact with hard tissue, wherein said first zone comprises one or more biomolecules affecting soft tissue and said second zone comprises one or more biomolecules affecting hard tissue.

For instance, the first zone may comprise biomolecules stimulating wound healing, such as VEGFs, PDGF, HGF, KGF, and FGF, and the second zone may comprise biomolecules stimulating mineral deposition, such as ameloblastin, poly-prolines, and collagens, or biomolecules stimulating bone attachment, such as extracellular matrix, CD molecules, integrins, and RGD-peptides. However, other combinations of biomolecules may also be employed.

It shall be noted that more than two zones, such as three or four zones, may be employed.

A further embodiment of the invention relates to a medical prosthetic device, such as a dental implant, comprising a first hydroxide layer having one or more biomolecules associated therewith, and a second hydroxide layer on top of the first layer, said second layer having one or more biomolecules associated therewith being different from the biomolecule(s) associated with the first layer. The biomolecule(s) associated with the second layer will, in vivo, be released before the biomolecule(s) associated with the first layer. The biomolecule(s) of the first and the second layer, respectively, may be selected such that the release is optimized with regard to the biological processes following implantation. It shall be noted that more than two layers, such as three or four layers, may be employed.

The invention is further illustrated by the following, non-limiting examples of which Examples 1, 2, 3, 5, 7 and 10 describe conducted experiments, and Examples 4, 6, 8, 9 and 11 illustrate contemplated working examples.

EXAMPLE 1

Preparation and Characterisation of a Titanium Hydroxide Layer

After carefully cleaning, specimens of Titanium Grade 2 coin-shaped electro-polished titanium implants with a surface area of 0.35 $cm^2$ were anodically polarized in a bath consisting of 0.5 M NaCl and 1 M NaOH. This was done at elevated temperature to obtain a suitable rate for the reaction between titanium and hydroxide forming titanium hydroxide.

A temperature of 80° C. was selected as the reaction temperature.

EXAMPLE 2

Testing of Titanium Implants Having Their Biocompatibility Improved by Electrolytic Incorporation of Hydroxide in the Surface Eight coin-shaped implants with a diameter of 6.25 mm were attached to an titanium electrode and submerged in a sterile electrolyte comprising 0.5 M NaCl adjusted to pH 8.0 by the use of 1.0 M NaOH. The electrode was attached to the positive outlet of a power supply, and an electrical current of 10 Volts at 100 mA was applied according to the setup in Example 1. The electrolytic process producing a thin layer of titanium hydroxide on the implant surfaces was allowed to continue for eight hours at 70° C. Eight further implants that were concomitantly present in the electrolyte, but not attached to the electrode, were also included as controls.

After electrolysis, the implants were cleaned in sterile water and subsequently placed in sterile glass containers where they were allowed to air-dry.

The implants with titanium hydroxide surfaces (n=8) and controls (n=8) were placed in calibrated cortical bone defects in the tibia of rabbits (New Zealand White). A small central fenestration into the bone marrow beneath each implant was made to allow for migration of osteogenic cells to the implant surfaces. The methods used were all according to a standardized and validated model established for the study of bone attachment to titanium implant surfaces (Ronold, H. J. and Ellingsen, J. E.: The use of a coin shaped implant for direct in situ measurement of attachment strength for osseointegrating biomaterial surfaces, Biomaterials 23, 2201-2209 (2002)). Each rabbit received four implants, two in each tibia bone. Locations of test and control implants were randomized and the operator was blinded.

Six weeks after implantation, the rabbits were sacrificed and the tibia bones with the implants attached were excised.

Directly after excision, the tibia bone was fixed in a specially designed jig, and the implants were detached using a calibrated pull-out procedure measuring the strength of the bonding between the implant and the bone. The force needed to detach the implants was recorded in Newton (N).

The results, (Table I), demonstrate that the titanium implants that have had their surfaces modified by electrolytic incorporation of hydroxide ions were significantly ($p<0.01$) more strongly attached to cortical bone than the control implants after six weeks of healing. This result is clinically important as early bone attachment is a sign of reduced bone healing time. This is important for successful clinical outcomes of "early loading" strategies in orthopedic and dental implant treatments.

TABLE I

| | Implant attachment assessed pull-out force needed to detach implants from bone measured in Newton (N) | |
|---|---|---|
| Implants | Controls (n = 8) [N] | Hydroxidized (n = 8) [N] |
| 1 | 9.9 | 39.6 |
| 2 | 11.6 | 29.0 |
| 3 | 7.3 | 44.8 |
| 4 | 15.1 | 11.6 |
| 5 | 13.6 | 26.4 |
| 6 | 11.2 | 6.2 |
| 7 | 1.7 | 6.9 |
| 8 | 2.4 | 17.7 |
| Mean values | 9.1 | 22.8 |

EXAMPLE 3

Preparation of a Titanium Hydroxide Implant Surface Layer Comprising an Extracellular Matrix Protein The set-up from example one was used to produce a layer of titanium hydroxide comprising the extracellular matrix molecule amelogenin onto electro-polished titanium implants with a surface area of 0.35 $cm^2$ exposed to the electrolyte. The electrolyte in both chambers was 1M NaCl in sterile water, pH adjusted to pH 8.5 by the use of NaOH, and the initial concentration of amelogenin was 0.1 mg/ml. For electrolysis a voltage of 10 volts at a charge density of 1 mA/$cm^2$ was used. $T_{an}$ was set to 70° C. Electrolysis was allowed to progress for 18 hours after which the titanium implants were removed from the electrolysis cell, washed in sterile water and allowed to air-dry in a desiccator.

After drying the titanium, specimens were washed three times in 1 ml saline at pH 6.5. Following the washes the proteins remaining on the titanium surfaces were dissolved by boiling the titanium specimen in 0,1 ml 2×SDS sample buffer (0.4 g SDS, 1.0 g 2-mercaptoethanol in 10 ml 0.125 M Tris/HCl, pH 6.8) for 5 minutes. The amount of amelogenin dissolved into the SDS solution from the rinsed titanium surfaces was then analysed by standard photometry measuring light absorbance at 280 and 310 nm against a 2×SDS sample buffer blank, and comparing the results with a standard dilution series of amelogenin in 2×SDS sample buffer. The experiment was repeated twice in series of 16 implants, both times with 5 negative internal controls in the form of identical titanium implants that was present in the reaction chamber during the whole process, but not attached to the anode.

This experiment clearly demonstrates that a significant amount of amelogenin was incorporated in the hydroxide layer during the electrolytic process. The amelogenin proteins were not only present as a simple coating, as there is no evidence of proteins in the washing solutions. Only with the combination of a strong detergent (SDS), a reducing agent (mercaptoethanol) and high temperature (100° C.) could amelogenins be extracted from the surface layer of the titanium hydroxide. The amount of protein extracted was calculated to range between 32 and 94 µg/cm$^2$ with a mean value of 67 µg amelogenin per cm$^2$ by comparison with the amelogenin standard. Identical control implants that had been present in the same electrolytic cell as the experimental implants, but that were not connected to the anode showed no amelogenin proteins attached to the titanium surface.

EXAMPLE 4

Preparation of a Titanium Hydroxide Implant Surface Layer Comprising a Synthetic Growth Factor-based Peptide The set-up from Example 3 can be used to prepare a layer of titanium hydroxide comprising a synthetic, full-length (37 amino acids) fibroblast growth factor 4 (FGF-4) peptide onto coin-shaped electro-polished titanium implants with a total surface area of 0.6 cm$^2$ exposed to the electrolyte. Electrolytes, pH, voltage, current density and electrolysis time may suitably be as in Example 3. The initial concentration of FGF-4 may suitably be 0.1 mg/ml, and the anode chamber temperature may suitably be 50° C.

Following washing in saline and 2×SDS-PAGE buffer, precipitation, centrifugation, re-dissolution in SDS-PAGE, boiling and electrophoresis protein in the gel may be transferred to a silver staining solution and the full-length synthetic FGF-4 peptides present visualised as a distinct band in the gel. Identical control implants present in the same electrolytic cell as the experimental implants, but not connected to the anode, can be used as controls.

EXAMPLE 5

Preparation of a Titanium Hydroxide Implant Surface Layer Comprising Nucleic Acid The set-up from Example 3 was used to produce a layer of titanium hydroxide comprising nucleic acids in the form of radio-labelled total human placenta DNA onto electro-polished titanium implants with a total surface area of 0.35 cm exposed to the electrolyte. The electrolyte in both chambers was 1M NaCl in sterile water. The pH was adjusted to pH 8 by the use of NaOH. The initial concentration of DNA in the electrolyte was 10 µg/ml. For electrolysis a voltage of 10 volts at a charge density of 1 mA/cm$^2$ and a $T_{an}$ of 65° C. were used. Electrolysis was allowed to progress for 16 or 24 hours after which the titanium specimens were removed from the electrolysis cell, rinsed three times in ample amounts of Tris-EDTA buffer (TE-buffer; 10 mM Tris-Cl and 1 mM EDTA in sterile water, pH 7,6) and then allowed to air dry over night in a desiccator.

The DNA was radio-labelled using Stratagene Prime-It® II Random Primer Labelling kit for production of high specific-activity probes and [α-$^{32}$P]dATP (Amersham). After labelling of DNA the specific radioactivity of the DNA probe was measured in a Packard Tricarb® scintillation counter to be 3,0×10$^8$ disintegrations per minute per microgram labelled DNA (dpm/µg).

After drying, the titanium specimens with tentative nucleic acids attached were placed on a phosphor screen (Fujii®) for 15 minutes. The specimens were then removed and the phosphor screen was scanned in a BioRad® phosphor imaging machine measuring the number of disintegrations occurred at the surface of each implant using a 100 µm grid (12,265 points per implant) The experiment was repeated twice in series of 16 implants, both times with 5 negative internal controls in the form of identical titanium implants that was present in the reaction chamber during the whole process, but not attached to the anode. For the first series the reaction time was 24 hours, for the second it was 16 hours. The total number of dpm per implant was the calculated and converted to µg DNA per square centimeter (µg DNA/cm$^2$).

This experiment clearly demonstrates that a significant amount of DNA was incorporated in the hydroxide layer during the electrolytic process. The DNA was not only present as a simple coating because the DNA was not dissolved or washed off the test implants during rinsing with TE. The amount of DNA present on the implants ranged between 0,15 and 0,55 µg/cm$^2$ with a mean value of 0,38 µg DNA per cm$^2$, when the reaction time was 24 hours. When reaction time was reduced to 16 hours the respective values ranged between 0,10 and 0,32 µg/cm$^2$ with a mean of 0,28 µg DNA per cm$^2$. This figure is well within the applicable range for gene therapy and DNA vaccines and other molecular medicine applications. Identical control implants that had been present in the same electrolytic cell as the experimental implants, but that were not connected to the anode showed only very small amounts (picograms) of DNA attached to the surface.

EXAMPLE 6

Preparation of a Biomineral-inducing Titanium Hydroxide Implant Surface Layer

The set-up from Example 3 may be used to prepare a layer of titanium hydroxide comprising a synthetic poly-proline peptide that has the potential to act as a biological nucleator of mineral formation in saturated solutions of calcium phosphate. The biomolecule may be incorporated in the hydroxide layer on electro-polished, coin-shaped titanium implants surface with a total area exposed to the electrolyte of 0.35 cm$^2$. The electrolyte in both chambers may suitably be 1M NaCi in sterile water with pH adjusted to pH 10 by means of NaOH, and the initial concentration of the synthetic poly-proline ma suitably be 0,1 mg/ml. For electrolysis a voltage of 10 volts at a current density of 1 mA/cm$^2$ and an anode chamber temperature of 40° C. may be used. Electrolysis may suitably be allowed to progress for 18 hours after which the titanium implants are removed from the electrolysis cell, rinsed in sterile water and allowed to air-dry in a desiccator.

After drying the titanium, implants and controls with tentative mineral nucleating peptide attached are placed in 5 ml saturated solution of calcium phosphate. After incubation for 4 hours in room temperature, the implants are removed from the mineral solution, rinsed in sterile water and air-dried in a desiccator. When dry, the implants may be directly submitted to scanning electron microscopy for assessment of the number of mineral foci present on the modified surfaces. Identical control implants present in the same electrolytic cell as the experimental implants but not connected to the anode may be used as controls.

EXAMPLE 7

Preparation of a Mineral-inducing Titanium Bio-hydroxide Implant Surface Layer

Eight coin-shaped implants with a diameter of 6,25 mm were attached to an titanium electrode and submerged in an sterile electrolyte comprising 0.5 M NaCl, adjusted to pH 8.0 by the use of 1.0 M NaOH, and a synthetic poly-proline peptide (pI =5.85), believed to stimulate nucleation of mineral crystals, at a final concentration of 0.01 mg/ml. The electrode was attached to the positive outlet of a power supply, and an electrical current of 10 Volts at 100 mA at a cell temperature of 40° C. was applied for eight hours according to the setup in Example 1. The electrolytic process produced a thin layer of titanium hydroxide with the synthetic peptide incorporated on the implant surfaces. Eight further implants that were concomitantly present is the electrolyte, but not attached to the electrode, were also included as controls.

After electrolysis the implants were rinsed in sterile water and subsequently placed in sterile glass containers where they were allowed to air-dry.

After drying the sterile peptide/hydroxide-modified titanium implants and controls were submerged in 50 ml of a saturated solution of calcium phosphate at 50° C. The solution was then allowed to cool to room temperature over a time period of 48 hours. The implants were removed from the mineral solution, rinsed briefly in sterile water and air-dried in a desiccator. When dry, the implants were analyzed directly by scanning electron microscopy (SEM) for quantitative and qualitative assessment of the number and nature of mineral precipitation foci present on their surfaces. The number of mineral forming units (mfu) on the surface corresponds directly to the number of mineral nucleation sites present on the surface during the experiments.

The results, (Table II), demonstrate that the titanium implants that have had their surfaces modified by electrolytic incorporation of synthetic poly-proline peptides molecules and hydroxide ions, have a significantly ($p<0.01$) increased number of mineral deposition foci. The deposited mineral had a high content of calcium and phosphor indicating that the depositions were all calcium phosphate. This is a strong indication that the electrolytic incorporation of hydroxide ions combined with a biomolecule can strongly influence bone mineral deposition onto implanted titanium surfaces in vivo. Metal implant surfaces that have the ability to induce and promote nucleation and deposition of bone mineral (calcium phosphates) onto their surfaces are likely to perform better clinically than other implants. An increased rate of bone mineral deposition onto the implant surface is believed to speed up osseointegration of the implant and stimulate the healing of the surrounding bone tissue. A proper osseointegration is considered the hallmark for successful clinical outcomes of orthopedic and dental implant treatments.

TABLE II

Number of mineral forming units (mfu) per square mm implant surface assessed by SEM. Values above 10 000 are recorded as "confluent"

| Implants | Controls (n = 8) [mfu] | Bio-Hydroxidized (n = 8) [mfu] |
| --- | --- | --- |
| 1 | 1225 | 8100 |
| 2 | 1936 | confluent |
| 3 | 2704 | confluent |
| 4 | 1369 | 5625 |
| 5 | 3844 | confluent |
| 6 | 5184 | 7744 |
| 7 | 1444 | confluent |
| 8 | 3249 | 9025 |
| Mean values | 2619 | >8812 |

EXAMPLE 8

Preparation of a Dual Layer Biomolecule-titanium-hydroxide Implant Surface

The set-up from Example 3 may be used to prepare a dual layer of biomolecule comprising titanium hydroxide on the surface of electro-polished, coin-shaped titanium implants with a total surface exposed to the electrolyte of 0.35 cm$^2$. The inner layer may be prepared using amelogenin as biomolecule according to the method in Example 3. Immediately after this procedure, and without air-drying in between, the electrolyte and conditions may be changed to those of Example 5 using genomic human DNA as biomolecule. In this way titanium implants may be prepared with an outer layer of titanium hydroxide-DNA over-laying an inner layer of titanium hydroxide-amelogenin. After the electrolysis the implants are removed from the electrolysis cell, rinsed in sterile water and allowed to air-dry in a desiccator.

After drying the titanium specimens with tentative nucleic-acids and proteins attached are suitably rinsed three times in Tris-EDTA buffer (TE-buffer; 10 mM Tris-Cl and 1 mM EDTA in sterile water). At each rinse the pH is increased starting at pH 7.4, then rinsed at pH 7.6 and finally at pH 8.0. After rinsing in TE the remaining DNA and protein on the titanium implants is finally removed using 0.1 N NaOH. The rinsing fractions are then divided in two; on part for nucleic acid analysis and one for protein analysis. The DNA fractions are suitably precipitated with an equal volume of absolute alcohol at −20° C. for 1 hour and then cleared from the supernatant by centrifugation at 13,000 g at 4° C. The pellet is then dissolved in 50 μl TE buffer pH 7.4 and the amount of DNA from all four rinsing solutions assessed by fluorometric analysis using Hoechst dye (Boehringer Mannheim).

The fractions for protein analysis are suitably precipitated with an equal volume of 0,6 N perchloric acid and the supernatants cleared by centrifugation. The precipitation pellets comprising salt and proteins are then dissolved in 50 μl 2×SDS-PAGE sample buffer (0.4 g SDS, 1.0 g 2-mercaptoethanol, 0.02 g bromophenol blue and 4.4 g glycerol in 10 ml 0.125 M Tris/HCl, pH 6.8) and boiled for five minutes. All samples are then submitted to electrophoresis on a 10% SDS-polyacrylamide gel at 80 mA for 4 hours. After electrophoresis proteins in the gel are transferred to a silver staining solution, and amelogenin present in the fractions is visualized as distinct bands in the gel.

Identical control implants present in the same electrolytic cell as the experimental implants, but not connected to the anode, may be used as controls.

EXAMPLE 9

Preparation of a Dual Zone Biomolecule-titanium-hydroxide Layered Implant Surface The set-up from Example 3 may be used to prepare two separate zones of titanium hydroxide layers. Electro-polished, rod-shaped titanium implants with a total surface area of 2 cm$^2$ were treated according to Examples 3 and 4. First the implants placed in the electrolyte from Example 3, so that only one half of each implant is submerged in the electrolyte. After the procedure of Example 1 is completed, the implants are turned upside down and placed in a new electrolyte similar to the one used in Example 4, so that the untreated half of each implant now is submerged in electrolyte. The procedure and reaction conditions from Example 4 are then carried out, after which the titanium specimen is removed from the electrolysis cell, rinsed in sterile water and allowed to dry in a desiccator.

Following electrolysis, the dual zone implants are cut in two at the centre. The halves layered with titanium hydroxide-synthetic FGF-4 peptide may be submitted to analysis according to Example 4. The other halves of the implants, layered with titanium hydroxide-amelogenin, may be analysed according to Example 3. Identical control implants present in the same electrolytic cells as the experimental implants but not connected to the anode may be used as controls.

EXAMPLE 10

Preparation of an Osteoinductive Titanium Hydroxide Implant Surface Layer Comprising a Biomolecule Eight coin-shaped implants with a diameter of 6.25 mm were attached to an titanium electrode and submerged in an sterile electrolyte comprising 0.5 M NaCl, adjusted to pH 8.0 by the use of 1.0 M NaOH, and amelogenin (a protein believed to stimulate wound healing and bone formation) at a final concentration of 1 mg/ml. The electrode was attached to the positive outlet of a power supply, and an electrical current of 10 Volts at 100 mA was applied for 16 hours at 60° C. according to the setup in Example 1. The electrolytic process produced a thin layer of titanium hydroxide with incorporated amelogenin on the implant surfaces. After electrolysis, the implants were rinsed in sterile water and subsequently placed in sterile glass containers where they were allowed to air-dry.

The eight hydroxidized implants from example 2 were included as control group.

The titanium implants with amelogenin/hydroxide-modified surfaces (n=8) and controls (n=8) were placed in calibrated cortical bone defects in the tibia of rabbits (New Zealand White). A small central fenestration into the bone marrow beneath each implant was made to allow for migration of osteogenic cells to the implant surfaces. The methods used were all according to a standardized and validated model established for the study of bone attachment to titanium implant surfaces (Ronold, H. J. and Ellingsen, J. E.: The use of a coin shaped implant for direct in situ measurement of attachment strength for osseointegrating biomaterial surfaces, Biomaterials 23, 2201-2209 (2002)). Each rabbit received four implants, two in each tibia bone. Locations of test and control implants were randomized and the operator was blinded.

Six weeks after implantation, the rabbits were sacrificed and the tibia bones with the implants attached were excised. Directly after excision, the tibia bones were fixed in a specially designed jig, and the implants were detached using a calibrated pull-out procedure measuring the strength of the bonding between the implant and the bone. The force needed to detach the implants was recorded in Newton (N).

The results, (Table III), demonstrate that the titanium implants that have had their surfaces modified by electrolytic incorporation of amelogenin molecules and hydroxide ions were significantly ($p<0.001$) more strongly attached to cortical bone than the control implants (only hydroxidized) after six weeks of healing. This result is clinically important as early bone attachment is a sign of reduced bone healing time. This is important for successful clinical outcomes of "early loading" strategies in orthopedic and dental implant treatments.

TABLE III

Implant attachment assessed pull-out force needed to detach implants from bone measured in Newton (N)

| Implants | Controls (n = 8) [N] | Bio-Hydroxidized (n = 8) [N] |
|---|---|---|
| 1 | 39.6 | 28.6 |
| 2 | 29.0 | 77.6 |
| 3 | 44.8 | 46.0 |
| 4 | 11.6 | 30.7 |
| 5 | 26.4 | 67.8 |
| 6 | 6.2 | 87.9 |
| 7 | 6.9 | 73.9 |
| 8 | 17.7 | 62.1 |
| Mean values | 22.8 | 59.3 |

EXAMPLE 11

Production of a Micro-rough, Mesoporous Titanium Hydroxide Surface with an Organic Inclusion Compound After carefully cleaning specimens of Titanium Grade 2 coin-shaped electro polished titanium implants with a surface area of 0.35 cm$^2$ are anodically polarized in a bath consisting of 0.5 M NaCl and 5 M NaOH. This is done at elevated temperature to obtain reaction condition for titanium hydroxide formation that morphologically modifies the surface topography. A temperature of 80° C. is selected as the reaction temperature, and the electrolysis is performed for 16 hours at 20 V. The micro-roughness is the analysed with atomic force microscopy and confocal laser scan microscopy. Porosity is assessed by scanning electron microscopy. The thickness of the titanium hydroxide layer can be determined by microscopy of metallographic cross sections. After hydroxidation the implant specimens are transferred to another electrolytic cell comprising amelogenin, in a set-up identical to the one used in example three. After additional electrolysis for 16 hours in this cell, the amount of protein in the modified titanium surface is assessed according to Example 3.

This experiment exemplifies the possibility of the method for producing a micro-structured, meso-porous titanium hydroxide surface with organic inclusions in a two-step procedure.

The invention claimed is:

1. A medical prosthetic device comprising a metal material having a surface,
    wherein the metal material is selected from the group consisting of titanium or an alloy thereof; zirconium or an alloy thereof, tantalum or an alloy thereof, hafnium or an alloy thereof, niobium or an alloy thereof and a chromium-vanadium alloy, wherein surface parts of the metal material comprises a layer of a corresponding hydroxide material selected from the group consisting of titanium hydroxide, zirconium hydroxide, tantalum hydroxide, hafnium hydroxide, niobium hydroxide, chromium hydroxide, vanadium hydroxide, and chromium-vanadium hydroxide, wherein said surface layer of hydroxide material comprises predominantly hydroxide in comparison to corresponding oxides, and wherein said hydroxide material comprises one or more biomolecule substances associated therewith, and wherein the biomolecule substance exhibits a net negative charge dissolved in a salt solution having a pH above 7.

2. The device as claimed in claim 1, wherein the metal material is titanium or an alloy thereof.

3. The device as claimed in claim 2, wherein the metal material is titanium.

4. The device as claimed in claim 1, wherein said surface parts of the metal material comprising the layer of the hydroxide material is adapted to be in contact with bone or other tissue when the device is deployed in the body of a mammal.

5. The device according to claim 1, wherein the device is selected from the group consisting of: a prosthetic femoral hip joint; a prosthetic femoral head; a prosthetic acetabular cup; a prosthetic elbow; a prosthetic knee; a prosthetic shoulder; a prosthetic wrist; a prosthetic ankle; a prosthetic hand; a prosthetic finger; a prosthetic toe; a prosthetic vertebra; a prosthetic spinal disc; a prosthetic cochlea; a prosthetic heart valve; and a prosthetic vessel.

6. The device as claimed in claim 5, wherein said prosthetic elbow implant is adapted to replace a stem, a wedge or an articular insert.

7. The device as claimed in claim 5, wherein said prosthetic knee implant is adapted to replace a femoral component, a tibial component, a stem, a wedge, an articular insert or a patellar component.

8. The device as claimed in claim 5, wherein said prosthetic shoulder implant is adapted to replace a stem or a head.

9. The device according to claim 1, wherein said device is sterile.

10. The device according to claim 1, wherein the biomolecule substance is selected from the group of substances consisting of: natural bio-adhesives; recombinant bio-adhesives; natural cell attachment factors; recombinant cell attachment factors; natural biopolymers, recombinant biopolymers; synthetic biopolyiners; natural blood proteins, recombinant blood proteins; natural enzymes; recombinant enzymes; natural extracellular matrix proteins; recombinant extracellular matrix proteins; natural extracellular matrix biomolecules; synthetic extracellular matrix biomolecules; natural growth factors; recombinant growth factors; natural hormones; recombinant hormones; natural peptide hormones; recombinant peptide hormones; synthetic peptide hormones; natural deoxyribonucleic acids; recombinant deoxyribonucleic acids; synthetic deoxyribonucleic acids; natural ribonucleic acids; recombinant ribonucleic acids; synthetic ribonucleic acids; natural receptors; recombinant receptors; enzyme inhibitors; drugs; biologically active anions; biologically active cations; vitamins; adenosine monophosphate (AMP), adenosine diphosphate (ADP); adenosine triphosphate (ATP); marker biomolecules; amino acids; fat acids; nucleotides (RNA and DNA bases); and sugars.

11. The device according to claim 10, wherein the biomolecule substance is interlocked, bound, trapped and/or integrated in or with the hydroxide material.

12. The device according to claim 11, wherein the layer of the hydroxide material comprises one or more biomoleculle substances in an amount from 1 picogram per $mm^2$ to 1 mg per $mm^2$.

13. The device according to claim 12, wherein the layer of the hydroxide material comprises one or more biomolecule substances in an amount of about 0.1 nanogram to 100 microgram per $mm^2$.

14. The device according to claim 11, wherein the biomolecule substance is non-covalendy interlocked, bound, trapped and/or integrated in or with the hydroxide material.

15. The device according to claim 10, wherein the layer of hydroxide material comprises one or more biomolecule substances in an amount from 1 picogram per $mm^2$ to 1 mg per $mm^2$.

16. The device according to claim 15, wherein the layer of the hydroxide material comprises one or more biomolecule substances in an amount of about 0.1 nanogram to 100 microgram per $mm^2$.

17. The device according to claim 1, wherein the biomolecule substance is interlocked, bound, trapped and/or integrated in or with the hydroxide material.

18. The device according to claim 17, wherein the layer of the hydroxide material comprises one or more biomolecule substances in an amount from 1 picogram per $mm^2$ to 1 mg per $mm^2$.

19. The device according to claim 18, wherein the layer of the hydroxide material comprises one or more biomolecule substances in an amount of about 0.1 nanogram to 100 microgram per $mm^2$.

20. The device according to claim 17, wherein the biomolecule substance is non-covalently interlocked, bound, trapped and/or integrated in or with the hydroxide material.

21. The device according to claim 1, wherein the layer of the hydroxide material comprises one or more biomolecule substances in an amount from 1 picogram per $mm^2$ to 1 mg per $mm^2$.

22. The device according to claim 21, wherein the layer of the hydroxide material comprises one or more biomolecule substances in an amount of about 0.1 nanogram to 100 microgram per $mm^2$.

23. The device according to claim 1, wherein said device is selected from the group consisting of: an artificial joint, a dental implant; an ossiculoplastic implant; a middle ear implant; a cocblear implant; an orthopaedic fixation device; a pacemaker; a catheter; a space filling implant; an implant for retention of a hearing aid; an implant for external fixation; an intrauterine device (IUDs); and a bioclectronic device.

24. The device as claimed in claim 23, wherein said prosthetic middle-ear implant is adapted to replace an incus, a malleus, a stapes, an incus-stapes, a malleus-incus, or a malleus-incus stapes.

25. The device as claimed in claim 23, wherein said orthaepedic fixation device is a nail, a screw, a staple or a plate.

26. The device as claimed in claim 23, wherein said bioelectronic device is an intracochlear or intracranial electronic device.

27. The device as claimed in claim 1, wherein the layer of hydroxide material has a thickness within the range of 1 nm to 50 μm.

28. The device as claimed in claim 27, wherein the layer of hydroxide material has a thickness equal to or above 0.5 μm.

29. The device as claimed in claim 27, wherein the layer of hydroxide material has a thickness within the range of 1 to 20 μm.

30. The device as claimed in claim 1, wherein the device comprises a first layer of hydroxide material without any biomolecule substance, and a second layer of hydroxide material comprising one or more biomolecule substances.

31. The device as claimed in claim 1, wherein the device comprises a first layer of hydroxide material comprising one or more biomolecule substances, and a second layer of hydroxide material on top of said first layer and comprising one or more biomolecule substances being different from the biomolecule substances of the first layer.

32. The device as claimed in claim 1, wherein the layer of hydroxide material comprises a first zone adapted to be brought into contact with soft tissue and comprising one or more biomolecule substances having an effect on soft tissue, and a second zone adapted to be brought into contact with hard tissue and comprising one or more biomolecule substances having an effect on hard tissue.

33. The device as claimed in claim 32, wherein the first zone comprises one or more biomolecules stimulating wound healing, and a second zone comprises one or more biomolecules selected from the group consisting of biomolecules stimulating mineral deposition and biomolecules stimulating bone cell attachment.

34. The device as claimed in claim 33, wherein the first zone comprises one or more biomolecule substances selected from the group consisting of VEGFs, PDGF, HGF, KGF, and FGF, and the second zone comprises one or more biomolecule substances selected from the group consisting of ameloblastin, polyprolines, collagens, extracellular matrix biomolecules, CD molecules, integrins, and RGD-proteins.

35. The device according to claim 1, wherein the biomolecule substance is selected from the group of substances consisting of biomolecules stimulating bone healing, biomolecules stimulating wound healing, biomolecules stimulating mineral deposition, biomolecules stimulating cell attachment, biomolecules stimulating cell proliferation and biomolecules stimulating cell differentiation.

36. The device according to claim 1, wherein the biomolecule substance is selected from the group of substances consisting of TGFs, BMPs, amelogenin, ameloblastin, VEGFs, PDGF, HGF, KGF, FGF, polyprolines, collagens, extracellular matrix biomolecules, CD molecules, integrins, RGD-peptides, growth factors, IL-6, osteocalin, osteoprotegrin, BSP and cytokines.

37. The device according to claim 1, wherein the biomolecule substance is selected from the group of substances consisting of biomolecules stimulating bone cell attachment, biomolecules stimulating osteoblastic cell proliferation and biomolecules stimulating osteoblastic cell differentiation.

38. A device as claimed in claim 1, wherein the biomolecule substance is present as an inclusion compound and/or trapped in or with the hydroxide material.

39. The device according to claim 1, wherein the biomolecule substance is selected from the group of substances consisting of: natural, recombinant or synthetic bio-adhesives; natural, recombinant or synthetic cell attachment factors; natural, recombinant or synthetic biopolymers, natural, recombinant or synthetic blood proteins; natural, recombinant or synthetic enzymes; natural, recombinant or synthetic extracellular matrix proteins; natural, recombinant or synthetic extracellular matrix bio-molecules; natural, recombinant or synthetic growth factors; natural, recombinant or synthetic hormones; natural, recombinant or synthetic peptide hormones; natural, recombinant or synthetic deoxyribonucleic acids; natural, recombinant or synthetic ribonucleic acids; natural, recombinant or synthetic receptors; natural, recombinant or synthetic enzyme inhibitors; natural, recombinant or synthetic peptides; natural, recombinant or synthetic proteins; natural or synthetic vitamins; adenosine monophosphate (AMP), adenosine diphosphate (ADP); adenosine triphosphate (ATP); amino acids; fatty acids; nucleotides (RNA and DNA bases); and sugars.

40. The device according to claim 1, wherein the biomolecule substance is a drug.

41. The device of claim 40, wherein the biomolecule substance is a stalin.

42. The device according to claim 1, wherein the biomolecule substance exhibits a net negative charge dissolved in a salt solution having an ionic strength within the range of from 0.01 to 10 M, a temperature within the range of from 0 to 100° C., and pH above 7.

43. The device according to claim 1, wherein the biomolecule substance is an ampholyte.

44. The device according to claim 1, wherein the biomolecule substance has an isoelectric (pI) point below 7.0.

* * * * *